United States Patent [19]
Liu et al.

[11] Patent Number: 5,691,633
[45] Date of Patent: Nov. 25, 1997

[54] METHOD OF AND APPARATUS FOR DETERMINING A PROPERTY OF A SAMPLE

[75] Inventors: Ying Liu; Eric William Abel, both of Dundee; Jill Janette Freda Belch, Scone, all of Scotland; Richard John Tweedie, Belfast, Northern Ireland

[73] Assignee: British Technology Group Limited, London, England

[21] Appl. No.: 374,659
[22] PCT Filed: Jul. 22, 1993
[86] PCT No.: PCT/GB93/01544
    § 371 Date: Apr. 7, 1995
    § 102(e) Date: Apr. 7, 1995
[87] PCT Pub. No.: WO94/02846
    PCT Pub. Date: Feb. 3, 1994

[30] Foreign Application Priority Data

Jul. 24, 1992 [GB] United Kingdom ............ 9215733

[51] Int. Cl.$^6$ ............................................. G01N 33/48
[52] U.S. Cl. ............................................. 324/71.1
[58] Field of Search ...................... 324/71.1, 71.2, 324/767, 719, 425, 263, 529, 71.5, 464, 461, 452, 453, 71.4, 71.3

[56] References Cited

U.S. PATENT DOCUMENTS

| | | | |
|---|---|---|---|
| 2,656,508 | 10/1953 | Coulter | 324/71.1 |
| 3,502,974 | 3/1970 | Coulter et al. | 324/71.1 |
| 3,793,587 | 2/1974 | Thom et al. | 324/71.1 |
| 3,801,904 | 4/1974 | Hogg et al. | 324/71.1 |
| 3,815,022 | 6/1974 | Golibersuch | 324/71.1 |
| 3,887,868 | 6/1975 | Guggenbuhl | 324/71.1 |
| 4,198,160 | 4/1980 | Kachel et al. | 324/71.4 |
| 4,296,373 | 10/1981 | Angel et al. | 324/71.1 |
| 4,420,720 | 12/1983 | Newton et al. | 324/71.4 |
| 4,434,398 | 2/1984 | Berg et al. | 324/71.4 |
| 4,438,390 | 3/1984 | Hogg | 324/71.1 |
| 4,791,355 | 12/1988 | Coulter et al. | 324/71.1 |

FOREIGN PATENT DOCUMENTS

| | | |
|---|---|---|
| 022568 | 1/1881 | European Pat. Off. . |
| 435166 | 7/1991 | European Pat. Off. . |
| 2298797 | 8/1976 | France . |
| 8803267 | 5/1988 | WIPO . |
| 9204630 | 3/1992 | WIPO . |

OTHER PUBLICATIONS

Proc. 10th. N.E. Bioenging. Conf., IEEE Press 1992, pp. 213–216, R. Schmukler et al "A New Transient Technique for Measurement of Isolated Cell Impedance".

*Primary Examiner*—Sandra L. O'Shea
*Assistant Examiner*—Roger Phillips
*Attorney, Agent, or Firm*—Cushman, Darby & Cushman IP Group of Pillsbury Madison & Sutro LLP

[57] ABSTRACT

An apparatus and method for determining a property of a sample, derived from a response obtained from the sample after an electrical pulse has been applied to it. Blood cells are subjected to an electrical pulse, a response is obtained using data retrieval means and a Fourier Transform is applied to the response. As the pulse applied is of very short duration (ideally a Dirac pulse) the Fourier transform yields information across a very broad bandwidth, typically several MHz, and accordingly a wide range of frequency response data is obtained. Certain cellular defects can be deduced from the transformed data. A detector is provided to detect precisely the presence of a cell as it passes through a particular region of an orifice. This is then used to trigger the pulse at a precisely controlled instant. This reduces the effect of random dispersion and can be adapted to ignore noise peaks which inevitably occur. The invention may be operated continuously and provides information across a bandwidth which is wider than was previously possible.

50 Claims, 7 Drawing Sheets

METHOD OF AND APPARATUS FOR DETERMINING A PROPERTY OF A SAMPLE

FIELD OF THE INVENTION

This application is a §371 of PCT/GB93/01544

This invention relates in general to a method of and apparatus for determining an electrical property of a sample and more particularly to a method of and apparatus for determining the impedance of particles such as biological cells (for example, white or red blood cells).

BACKGROUND OF RELATED ART

An increased awareness of the altered cell structure in vascular diseases and cancers has led to the development of techniques for the analysis of cell structure parameters. Changes in the characteristics of the cell membrane or nucleus are characteristic of several disorders. It has been found that the electrical properties of a cell can provide details of the composition and dimensions of the cell and more particularly of changes in the characteristics of the cell membrane and nucleus. Electrical activity in cells is due to the exchange of ions across cell membranes, which gives rise to potential differences and characteristic impedances. An advantage of determining the properties of cells from their electrical characteristics is that the characteristics of individual cells can be determined.

It is known from a paper by Schmukler, R. et al. ("A New Transient Technique for Measurement of Isolated Cell Impedance", Proc. 10th N.E. Bioenging. Conf., IEEE Press, 213-216) to determine the impedance characteristics of blood cells by embedding them in a polycarbonate filter, applying a current step stimulus to the system including the filter and cells embedded therein, and detecting the transient response to the step. The impedance characteristics (and hence various properties of the cells) are then determined from the transient response.

This known technique suffers from the drawbacks firstly that data processing of the transient response to a step stimulus can be complicated, secondly that it does not permit continuous tests to be carried out on a population of cells, and thirdly that it is time-consuming and expensive (in particular, the filter requires frequent replacement). Thus the technique is basically a laboratory technique, incapable of use in clinical tests.

International Patent Application WO 88/03267 describes a device which uses multiple AC sources to determine impedance of a sample at several frequencies. The orifice through which the samples flows, forms part of the oscillator tuning circuit. Therefore the oscillator output is dependant upon the orifice impedance. To allow multiple oscillators and a DC current source a novel method of coupling to the orifice must be used. The device described suffers from two main drawbacks. Firstly cells are measured at discrete frequencies therefore the frequency response of the cell is poor. Secondly the design is very complex. This complexity results from the requirement for a multichannel front-end and the coupling mechanism.

U.S. Pat. No. 3,887,868 describes a simple device which counts the number of particles and uses a logic circuit to determine the average cell volume. There is no provision for measuring the AC characteristics of the cells.

EP 022,568 describes what appears to be a modification to the counter previously described and produces a new flow chamber which can prevent bubbles entering the orifice. This device does not measure the AC characteristics of the cell.

U.S. Pat. No. 4,296,373, indicates that the changes to the basic counter are to facilitate different particulate sensing zones for different size particles.

EP 0,435,166 describes a particle counting and size device which attempts to solve the problem of the coincident passage of cells. This is achieved by using a laser as the sensing element. No High Frequency measurements are made.

U.S. Pat. No. 4,438,390 describes a simple extension of an existing counter to improve the Signal to Noise Ratio mechanically. Summing several pulses together is a well known averaging technique for improving low level signal in signal processing. As the cell can only be used once several sets of electrodes allow the same effect as repeating the experiment. The delay lines provide a very simple method of summing the result. This device does not measure the high frequency characteristics of the cell.

U.S. Pat. No. 4,055,799 describes a crude method of detecting the properties of a cell. Only one cell can be measured at a time as the diameter of the constriction is less than that of the cell therefore cells are trapped filling the constriction and restricting the current paths to those that pass through the cell. The pulses generated and responses obtained do not provide any frequency information; hence a spectrum cannot be generated. The amplitude of the pulse and the current density through the cell must exceed the limit of stimulation therefore the response of the cell can no longer be described as passive or linear. Several pulses are used, the pulses having a gradually increasing amplitude to determine electrical breakdown.

A problem with the device described in U.S. Pat. No. 4,055,799 is the removal of the cells at the end of each test.

U.S. Pat. No. 4,420,720 describes a method of generating shaped electric fields within an orifice. The electric field can be squeezed to produce a slit like field shape. This method would require the presence of a steady state field at a single frequency to ensure a stable field shape. Hence this system would have a high Signal to Noise Ratio and may be able to sense the single frequency characteristics of a small area of the cell. However, this response is still only an average of all the components in the sensing area. This device does not improve upon the ability to discriminate the impedance characteristics. The number of electric fields present and the need to control these fields to produce a sensing zone make this technique difficult to implement.

International Patent Application WO-A-9204630 appears to describe a technique for measuring non-linear characteristics of cells in a bulk volume of liquid. However, it is not apparent whether the technique and associated apparatus actually measures characteristics of the cells or non-linearity in the component electrodes. Input signals are sinusoidal, whereas in the present invention input signals are narrow pulses.

SUMMARY OF THE INVENTION

The present invention seeks to overcome the problems and provide an improved technique of determining the property of a sample.

According to the present invention, there is provided a method of determining a property of a sample, comprising applying an electrical pulse to the sample, detecting the response to the pulse, applying a transform to the detected response and determining a property from the transformed response.

According to another aspect of the present invention there is provided a method of determining a characteristic of a cell by applying an electrical pulse to the cell; detecting a response and determining an electrical property of the cell from the response.

The present invention allows cells to flow unimpeded through a constriction such as an orifice. This allows a large number of cells to be investigated rapidly and prevents a high current density in the individual cell. Therefore the response is linear and passive. The responses can be related to the resistance and capacitance of the cell.

According to a further aspect of the present invention above there is provided apparatus for determining a property of a sample comprising means for applying an electrical pulse to the sample, means for detecting the response to the pulse, means for applying a transform to the detected response and means for determining a property from the transformed response.

According to yet a further aspect of the present invention there is provided apparatus for determining an electrical characteristic of a cell comprising means for applying an electrical pulse to the cell; means for detecting a response and means for determining electrical characterization from the response.

This arrangement can afford the advantage of simplicity, in that it is relatively easy to determine say an electrical property, such as the impedance of the sample or cell, from the response to a pulse, as is demonstrated later.

According to yet further aspects of the present invention there is provided a method of determining an electrical property of a sample, comprising applying an electrical pulse to the sample, detecting the response to the pulse, and determining the electrical property from the response.

Further, as distinct from techniques where the stimulus is at a single frequency, a pulse of suitably short duration can stimulate a response over a wide band of frequencies. This can provide more information on the characteristics of the sample than would be obtained from a single frequency stimulus. For instance, if the sample is a blood cell, it may provide information not only on cell size but also on other cell characteristics such as abnormalities. This is because the various components of the cell structure, such as interfaces between membranes and electrolytes, contribute relaxation time constants to the response according to their impedance characteristics which may be different if cell abnormalities are present. A single frequency technique cannot analyze these relaxation times.

Preferably, the pulse is applied and the response is detected by an electrode arrangement and the sample is transported relative to the electrode arrangement, possibly in an electrolyte. By transporting the sample relative to the electrode arrangement, continuous, rapid and automatic tests can be carried out on a population of cells, so that large numbers of samples can be examined in a few seconds. Application of a pulse (of suitably short duration) can ensure that the sample is excited during the possibly short time for which the sample may be in the measurement zone (defined by the electrode arrangement). Furthermore, if the sample actually moves during application of the pulse, use of a pulse of suitably short duration can ensure that the sample may be considered, as far as analysis of the response is concerned, as being stationary for the duration of the pulse. A step stimulus (as taught in the prior art) would not suffice because it has to be applied over a relatively long time and this yields inaccurate results. Therefore a preferred pulse is in the form of an impulse function such as Delta Dirac or Dirac pulse. However, other types of pulses may be used. These may for example take the form of a "chirp" whose frequency characteristics and components, as well as duration, have been carefully tailored by preforming, or other techniques, so as to excite a sample over a specific waveband.

Such a technique enables a response of a sample to be measured over a known range of frequencies.

Preferably, the position of the sample relative to the electrode arrangement is detected, and the pulse is applied in dependence on the detected sample position. Since it is envisaged that the sample may be transported quite quickly, detection of the position of the sample may be useful in ensuring that the pulse is fired when the sample is in the desired location.

Means can be provided to detect a sample and provide or signal as to when the sample is at a position or within a particular region. This signal may be used to trigger or initiate a pulse. Preferably a peak detector is used to observe a voltage peak and processing means is used to calculate the instant of the maximum value of the peak by determining when the gradient of the peak approaches zero. Accordingly, by using this technique, the application of the pulse can be precisely controlled and errors arising from random spatial variation of a sample are minimized. Thus fewer tests need to be carried out on, for example, a blood cell passing through an orifice in order to obtain an average, as the trigger instant of the pulse applied to the cell can now be precisely controlled. This aspect can be incorporated to enhance the method of sample analysis.

Threshold selective triggering control may be provided so as to trigger the pulse at the peak voltage obtained from the position detector and not on some random noise peak, discontinuity in electrolyte fluid which may arise or other interference which could occur.

In a preferred embodiment, the sample is a particle, an orifice is provided through which the particle is transported, and the electrode arrangement is so located as to enable the pulse to be applied to the particle as the particle is transported through the orifice. Passing the particle (e.g. blood cell) through an orifice is advantageous since it can enable a particularly accurate determination of the impedance of the particle. Because the pulse is applied for only a short duration, typically between 50 ns and 1 μs, there is insufficient chance for any change to build up and cause distortion of measurements due to polarizations of the or each electrodes.

The pulse may be a voltage or current pulse. Its duration is suitably less than 20%, preferably less than 10%, of the duration of the transportation of the particle through the orifice. The shorter the duration of the pulse, the closer it will approximate to an impulse (dirac function), and the easier will become the analysis of the response, as is explained later. The amplitude of the pulse is limited by the requirement that the particle (cell) is not significantly damaged by the pulse.

If the response to the pulse includes a component due to the sample itself and a component due to influences external to the sample (such as the impedance of the orifice), then preferably responses to the pulse are determined both in the absence and in the presence of the sample, and the component due to the sample is determined from the difference between these two responses. This may, for example, be achieved using a model of the behaviour of the external influences (e.g. orifice). However, in the preferred embodiment, it is achieved by carrying out simultaneous tests using a live and a reference orifice arrangement, the same pulse being applied to both orifice arrangements. In this way the response purely from the sample can be determined to a high degree of accuracy.

It has been discovered pursuant to the present invention that a conventional orifice, such as the Coulter orifice (see U.S. Pat. Nos. 2,656,508 and 3,502,974), can have a substantial stray, distributed capacitance between its electrodes, and that further this stray capacitance can cause the orifice to have a rather limited bandwidth (say 100 kHz). Therefore, according to an aspect of the present invention which may be independent of its other aspects, in order to reduce the magnitude of this scatter capacitance, material having a low dielectric constant may be interposed between electrodes of the electrode arrangement. The ratio of the thickness of the material to the distance between the electrodes is preferably greater than 25%, more preferably greater than 50%. In another possibly independent aspect, the total area of an electrode pair of the electrode arrangement may be raised independently or in conjunction with the separation of the electrodes of the electrode pair. The effective total area of electrodes compared with the separation of electrodes may be less than 500 (area units): 1 (length unit) and preferably less than 100 (area units): 1 (length unit). With these features, it may be possible to increase the bandwidth of the orifice to 4–5 MHz.

Apparatus analogous to the method and incorporating one or more of the preferred features described above is also provided by the present invention.

If it is desired to reduce noise by providing apparatus with separate "input" (pulse application) and "output" (response detection) electrodes, preferably the apparatus includes a respective electrode mounted at each end of the orifice, these electrodes forming part of the detecting means. This leads to a particularly simple construction.

Data storage means may be provided in which a standard response and/or standard results are stored in an electronic form. Automatic comparison may be carried out by digital processing means. The data storage means may be electronic and could be connected to the output of the means performing the transform on the response. Such an arrangement allows for automatic data retrieval and comparison so as to facilitate or assist in determining certain characteristics of the sample. Apparatus incorporating such arrangement could for example assist in reading a rapid diagnosis of unhealthy blood cells. Additionally or alternatively other types of non-biological material(s) may be present in the sample. These materials may also be subjected to analysis.

BRIEF DESCRIPTION OF THE DRAWINGS

Preferred features of the invention will now be described, by way of example only, with reference to the drawings, in which.

DESCRIPTION OF PREFERRED EMBODIMENTS

Figure 1:
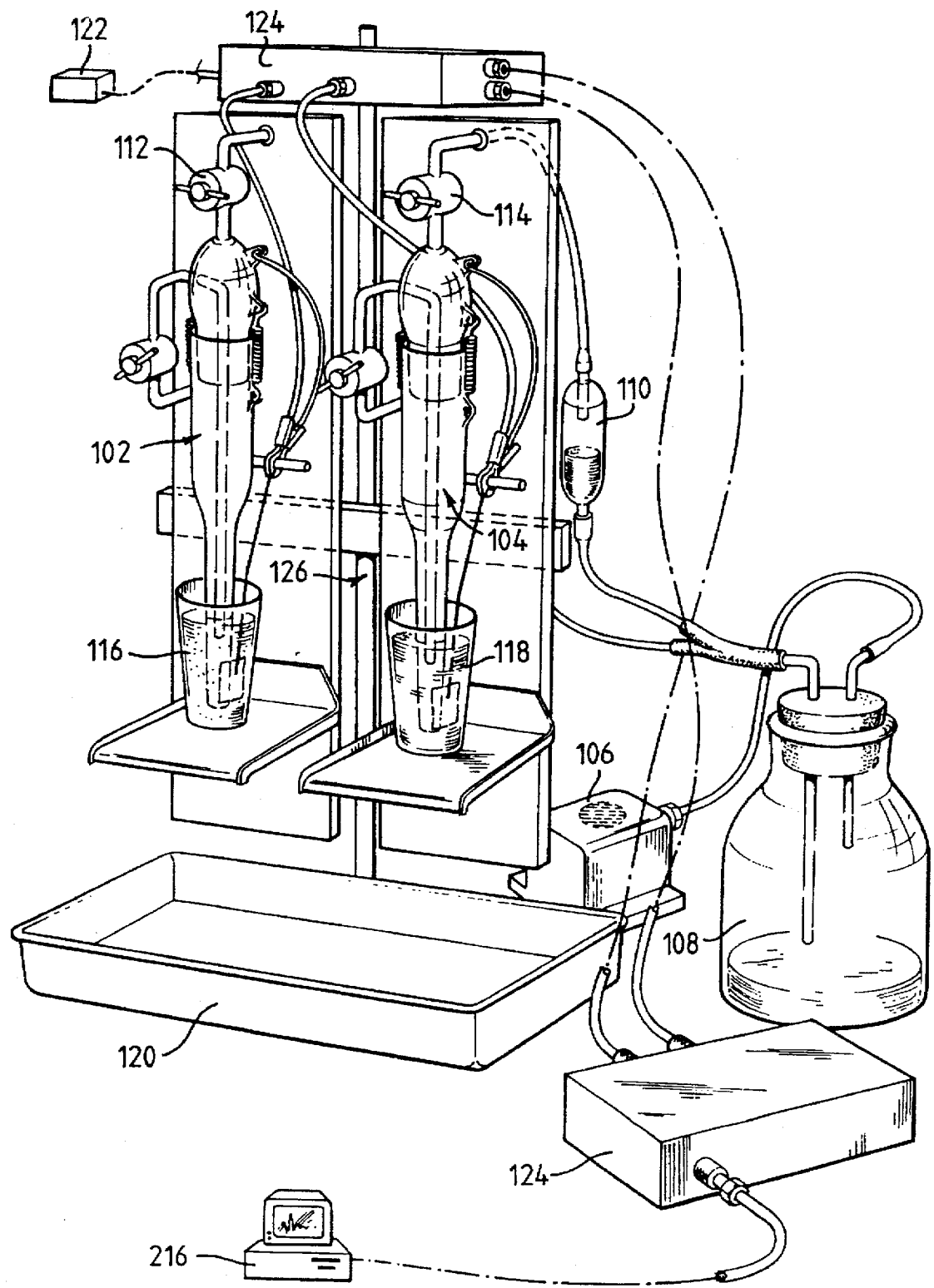
FIG. 1 is an overall sketch of apparatus for determining the impedance characteristics of a cell.

Referring to FIG. 1, apparatus for determining the impedance characteristics of a cell comprises generally live and reference test devices 102 and 104, a fluid handling arrangement including a pump 106, a waste container 108, a fluid trap 110, control valves 112 and 114, containers 116 and 118 and a drip tray 120, an electrical system including a low voltage supply typically 50 volts, 122 and control circuitry 124, and a framework 122 for this equipment. Advantages of using low voltages are that less noise is produced and there is less risk of damage occurring to the cell. Container 116 contains the sample (cells) in an electrolyte, whilst container 118 contains Just the electrolyte.

Figure 2:
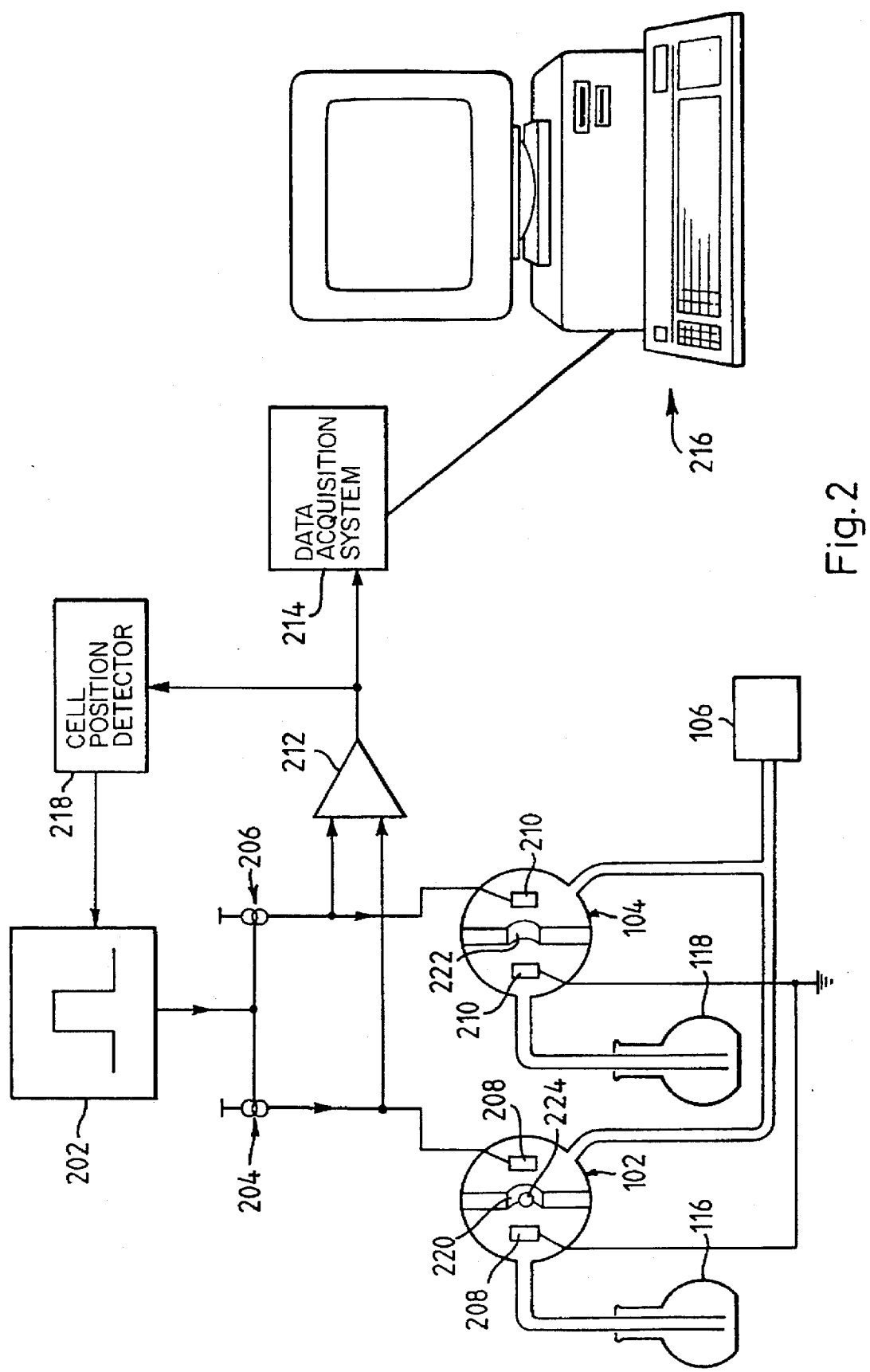
FIG. 2 is a block diagram of the electrical system of the apparatus.

Referring to FIG. 2, the electrical system includes a pulse generator 202 for applying an electrical pulse to the live and reference test devices 102 and 104 via respective constant current sources 204 and 206 and respective electrode arrangements 208 and 210. The control circuitry 124 includes a wideband differential amplifier 212 whose respective inputs are connected to the electrode arrangements 208 and 210, a data acquisition system 214 connected between the output of the differential amplifier 212 and a computer 216, and cell position detector circuitry 218 connected between the output of the differential amplifier 212 and the pulse generator 202. The live and reference test devices 102 and 104 include respective orifices 220 and 222 and are arranged to have identical electrical and hydrodynamic characteristics. A cell 224 is shown in FIG. 2 passing through the orifice 220.

Referring now to FIGS. 1 to 3, in broad terms, the invention functions as follows. The pump 106 pumps under negative pressure to the waste container 108 on the one hand the mixture of electrolyte and cells contained in container 116 through orifice 220 and on the other hand electrolyte from container 118 through orifice 222. Constant current sources 204 and 208 pass a constant direct current to the respective electrode arrangements 208 and 210. As the cell 224 begins to enter the orifice 220 (Stages (1) to (2), FIG. 3(a)), a signal is detected from the electrode arrangements by the differential amplifier 212 and amplified (FIG. 3(b)). This amplified signal is sent for processing to the cell position detector circuitry 218. If the signal is characteristic of a cell entering the orifice, the detector circuitry 218 triggers the pulse generator 202 to apply a pulse of short duration to the electrode arrangements 208 and 210 to coincide with the passage of the cell through the orifice 220 (Stage (2), FIG. 3(c)).

Electrode arrangement 208 picks up the response to the pulse due not only to the cell but also to the test device (most notably the electrolyte and the orifice 220); electrode arrangement 210 picks up the response due only to the test device. Differential amplifier 212 serves to subtract the two types of response to provide at its output an amplified signal solely (or largely) representative of the response due to the cell (FIG. 3(d)). This amplified signal is passed via the data acquisition system 214 to the computer 216 for storage, processing and display. In particular, the computer 216 performs a Fast Fourier Transform on the response to provide spectral response information (FIG. 3(e)). Other types of transforms such as a Hanley transform may be used. Similarly elaborate signal processing may be employed to carry out manipulation of data retrieved. such processing techniques may for example permit curve fitting to original time domain response data and/or amplify characteristics which require more complicated data processing algorithms. The response is modelled as a convolution of the electrical characteristics of the cell and the test device. The electrical characteristics of the cell are determined from the overall response using a predetermined model of the response of the test device. In the particular example of FIGS. 3(d) and 3(e), the cell response is illustrated as having two time constants, $t_1$ and $t_2$.

It should be noted that, with reference to FIG. 2, there is a potential risk of oscillation in the system if the loop comprising the test devices 102 and 104, the differential amplifier 212, the cell position detector circuitry 218, the pulse generator 202 and the constant current sources 204 and 206 is closed. In this embodiment, this problem is obviated by the use of a lockout circuit (see FIG. 7(b), discussed later).

It will be understood that noise can be a problem with the present invention. The major sources of noise are:
Johnson—thermal noise in semiconductors;
Shot—current noise in all components;
Partition—due to the thermocouple effect;
Power supply—mains ripple and current spikes;
Electromagnetic interference—Radiofrequency radiation from external sources; and
Hydrodynamic—due to the electrolyte in the orifice.

Measures may need to be taken to minimize noise. For example, low noise operational amplifiers should be used wherever feasible.

The apparatus should ideally have a bandwidth extending from direct current to at least 4 MHz, if not 10 or even 50 MHz, if all the cell characteristics are to be fully determined. The low frequency end is limited by the measurement rate. If the measurement rate is 2000 cells per second, the low frequency end is estimated at 20 kHz (assuming the measurement interval is ten times the sensing time). The high frequency end is limited by the rise time of the excitation pulse and the bandwidth of the electrical system and in particular the orifice.

The various major components of the apparatus are now described in more detail.

The Test Devices (102 and 104)

As shown in FIG. 1, the test devices are conventional COULTER (Trade Mark) cell flow cytometers having 100 μm orifices. As the orifice is so small and thus the ratio of cell to orifice diameter is quite significant (e.g. 1:10), the cell displaces a significant amount of electrolyte in the orifice. The conductance of the electrolyte is arranged to be different from that of the cell, so that the electrical characteristics of the system change significantly when a cell enters the orifice. The electrolyte is a conventional isotonic buffer, in which the cells are suspended in such dilution that the characteristics of individual cells may be detected as the cells pass through the orifice.

The live and reference test devices 102 and 104 have, as nearly as is practicable, the same electrical and hydrodynamic properties.

Figure 4:
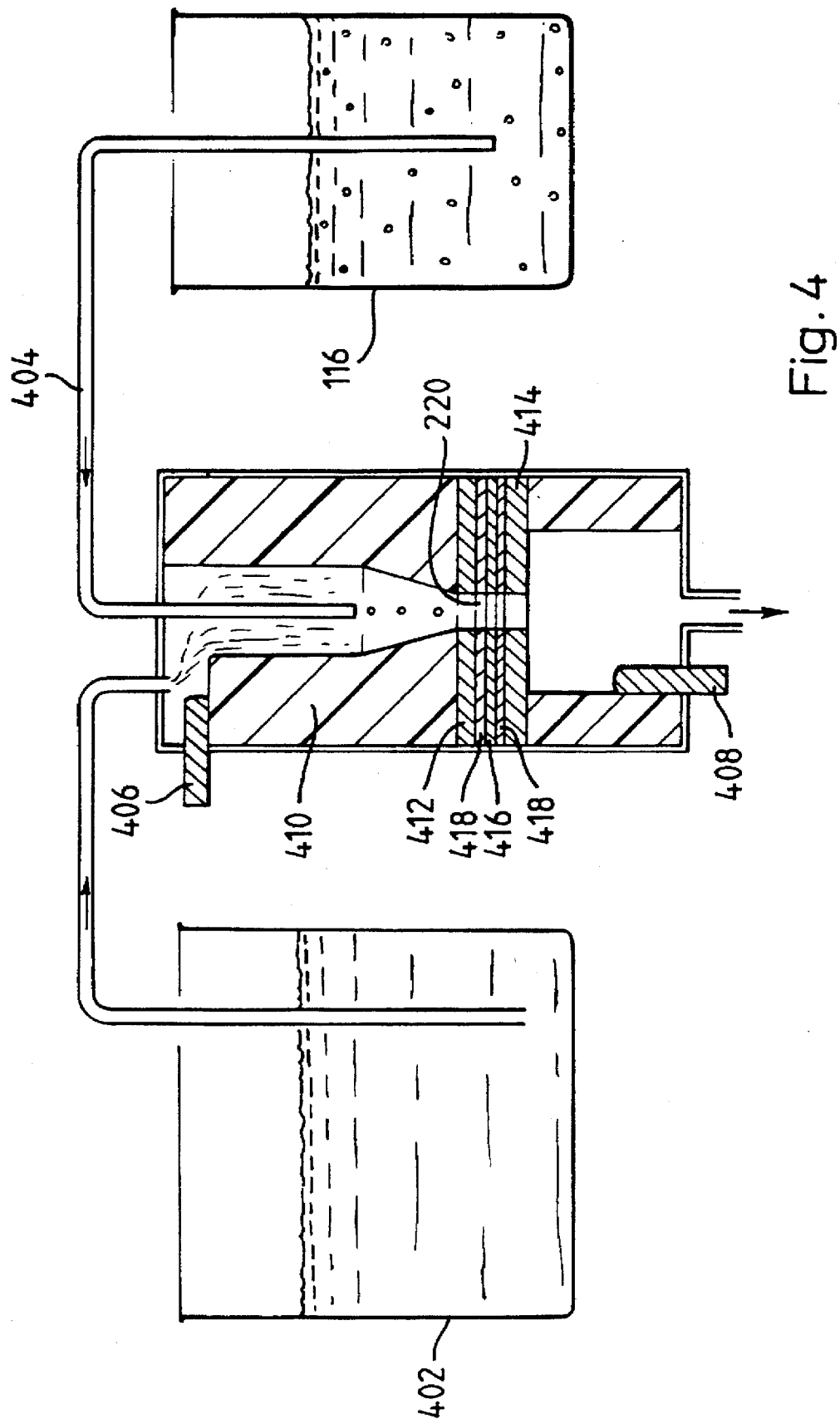
FIG. 4 is a sectional view of an alternative embodiment of apparatus employed in the present invention.

An alternative embodiment of test device is shown in FIG. 4. The device incorporates several features to improve its sensitivity. In order to afford a hydrodynamic focussing of the cell in the center of the orifice 220, a further container 402 is provided, containing just electrolyte; this container is maintained at a higher pressure than container 116. The flow from feed pipe 404 from container 116 is arranged to be "sheathed" by flow from container 402, thus enabling a precise centering of cells as they enter the orifice and also a control over the rate at which the cells enter the orifice.

The two platinum electrodes 406 and 408 via which the pulses are applied to the cell/electrolyte mixture are separated by a material 410 of low dielectric constant (especially at high frequency) which forms the walls defining the chamber leading to the orifice. A suitable material is polystyrene (e.g. POLYPENCO (Trade Mark) with a dielectric constant of 2.54). Use of such a material reduces scatter capacitance and thereby allows measurements to be made over a much larger bandwidth.

The two platinum electrodes 412 and 414 via which the response to the pulse is detected form part of the orifice assembly itself. Using a four electrode rather than two electrode system renders the test device more sensitive. The electrodes 412 and 414 are relatively small in diameter (e.g. 3-4 mm), again in order to reduce scatter capacitance. Instead of the electrodes being mounted at each end of the orifice, they could be mounted in opposing configuration in the wall of the orifice, flush with that wall. This might yield a more sensitive detection system.

The orifice assembly is made using semiconductor fabrication techniques and comprises a silicon or sapphire substrate 416, optional insulating layers 418 deposited thereon and the electrodes 412 and 414 deposited on the insulating layers. The orifice is made using a conventional etching technique, and has a diameter of 100 μm and a length of 250–300 μm. Other techniques for making the orifice, such as laser drilling, are possible. The substrate 416 and insulating layers 418 have a relatively low dielectric constant, again to reduce scatter capacitance.

Instead of the orifice assembly being made using semiconductor fabrication techniques, an orifice assembly comprising a sapphire crystal (having a central bore as the orifice) and a mounting for the crystal could be used. A hole for the orifice may be formed by a laser in a silicon wafer. This enables a variety of small electronic components such as amplifiers to be directly fabricated onto the silicon within very close proximity of the orifice by conventional semiconductor chip fabrication techniques. Track lengths can be designed to minimize capacitance coupling and leakage and this too reduces noise. Suitable combinations of silicon dioxide ($S_iO_2$) and amorphous silicon can be used to insulate the chip so that it can be immersed in solutions. In general $S_iO_2$ is chemically inert. However, other semiconductor materials could be used in hazardous chemical environments.

The Pulse Generator (202) and Constant Current Sources (204, 206)

In the design of the pulse generator 202, the following design considerations need to be taken into account. The duration of the pulse should be less than (preferably considerably less than) the duration of the cell in the orifice (25 to 50 μs in the present embodiment, most usually 26 to 30 μs). A long pulse (say, of 25 μs) provides a large excitation energy and therefore high signal to noise ratio, but reduces the accuracy of the apparatus because the cell moves during the pulse a significant distance through the non-uniform electric field in the orifice. If the pulse is sufficiently short, the movement of the cell in the aperture is negligible, although this is at the expense of a lower signal to noise ratio. It may be possible to dispense with the requirement that the pulse be sufficiently short that the movement of the cell in the aperture is negligible. Corrections for the movement of the cell could instead be made, or the system could be calibrated for such movement.

The current (or voltage) pulse should be as high as possible within the limitation that the pulse does not damage the cell so significantly that its characteristics are altered. This limitation needs to be determined experimentally.

In the present embodiment, a pulse of 2 to 5 μs width and 0.5 to 5 mA amplitude, and in particular 2 μs width and 3 mA amplitude, has been found to be satisfactory.

The pulse should be as near as possible a true direct current impulse (that is, a true "square" wave). In particular, it needs fast rise and fall times on the order of 20–40 ns. A bipolar transistor operated in its quasi-saturation region has been found to be a suitable device for fulfilling these requirements.

Figure 5:
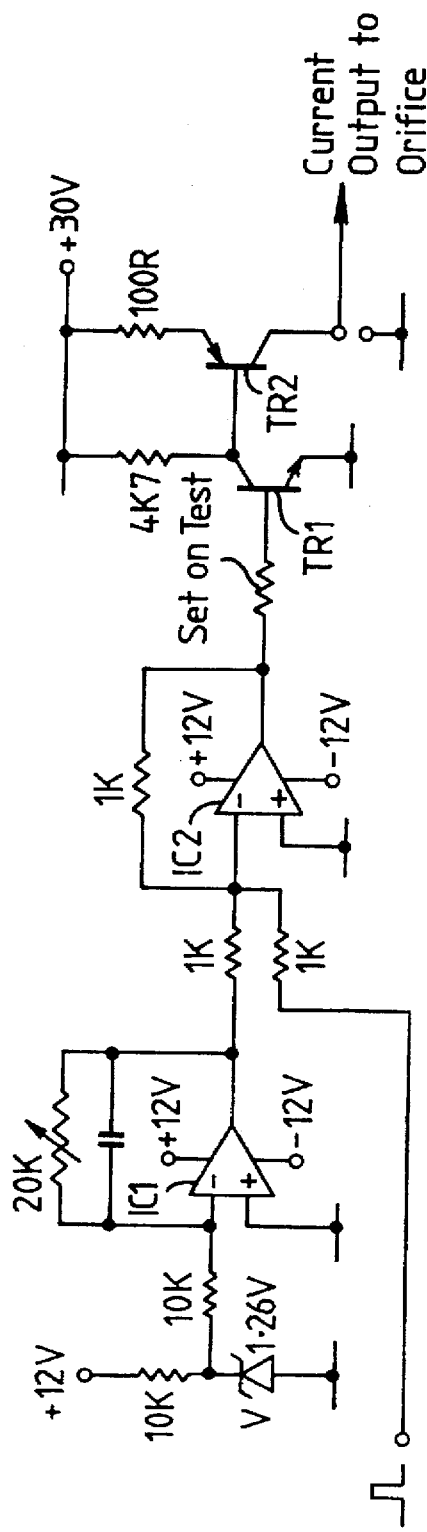
FIG. 5 is a circuit diagram of a pulse generator and constant current source employed in the present invention.

A suitable pulse generator circuit, which also serves as the constant current sources 204, 206 for the initial detection of the cell, is shown in FIG. 5. The circuit includes a precision voltage reference D, operational amplifiers IC1 and IC2 together with appropriate circuitry, and bipolar NPN and PNP transistors TR1 and TR2 respectively, again together with appropriate circuitry. Operational amplifier IC1 provides a constant but variable reference voltage at its output. The low level constant current produced by the circuit can be controlled by adjusting the gain of operational amplifier IC1. In this embodiment, the current is set at 0.2 mA. Operational amplifier IC2 acts as an adder amplifier to determine the current output of transistor TR2 via transistor TR1. The excitation pulse is triggered at an input of IC2 by a trigger pulse from the cell position detector circuitry 218. All the operational amplifiers are low noise devices.

It will be appreciated that circuitry analogous to that shown in FIG. 5 could be employed to produce a constant voltage and a voltage pulse.

Figure 8:
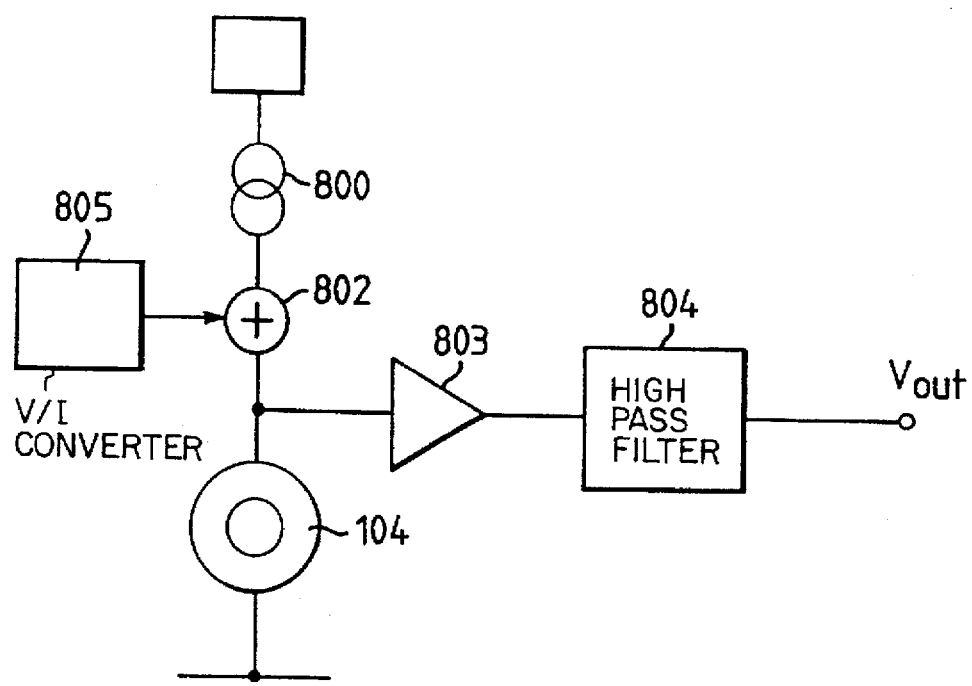
FIG. 8 is a block diagram of an alternative embodiment of pulse generator and constant current source.

An alternative embodiment of pulse generator and constant current source is shown in FIG. 8. This comprises a constant current source 800 which is an active device using JFETS to minimize noise, a voltage to current converter 801 which converts a trigger pulse from the cell position detector circuitry 218 into a current pulse and adds it to the current produced by current source 800 at adder 802, a low gain amplifier 803, and a high pass filter 804, as well as the test device 104. Use of JFETS provides the advantage of enabling lower direct current supply voltages to be obtained and hence smaller input noise. The voltage to current converter 805 is designed to be completely off when no pulse is present, and hence contributes no noise to the system when there is no pulse. On receipt of a voltage pulse, a current of known amplitude is produced. The voltage amplifier 803 of FIG. 8 is of low gain (Gain=1) due to the large direct current component. High pass filtering removes this component before differential amplification by the differential amplifier 212. Placement of the high pass filter after the amplifier 803 ensures that the capacitance at the orifice of the test device is kept to a minimum and that the network does not load the orifice.

It may be desirable to incorporate the two test devices 102 and 104 into a true bridge configuration, with the other two arms of the bridge being provided by suitable impedance loads. However, it is important to balance or very nearly balance the bridge over the complete frequency spectrum of interest. Some variation to the power supply will be required. However, it will be appreciated that a variety of combinations of variables exist. For example by keeping the current constant and varying the voltage and vice versa. Complicated processing may be required to extract data from a broad frequency spectrum.

Figure 9:
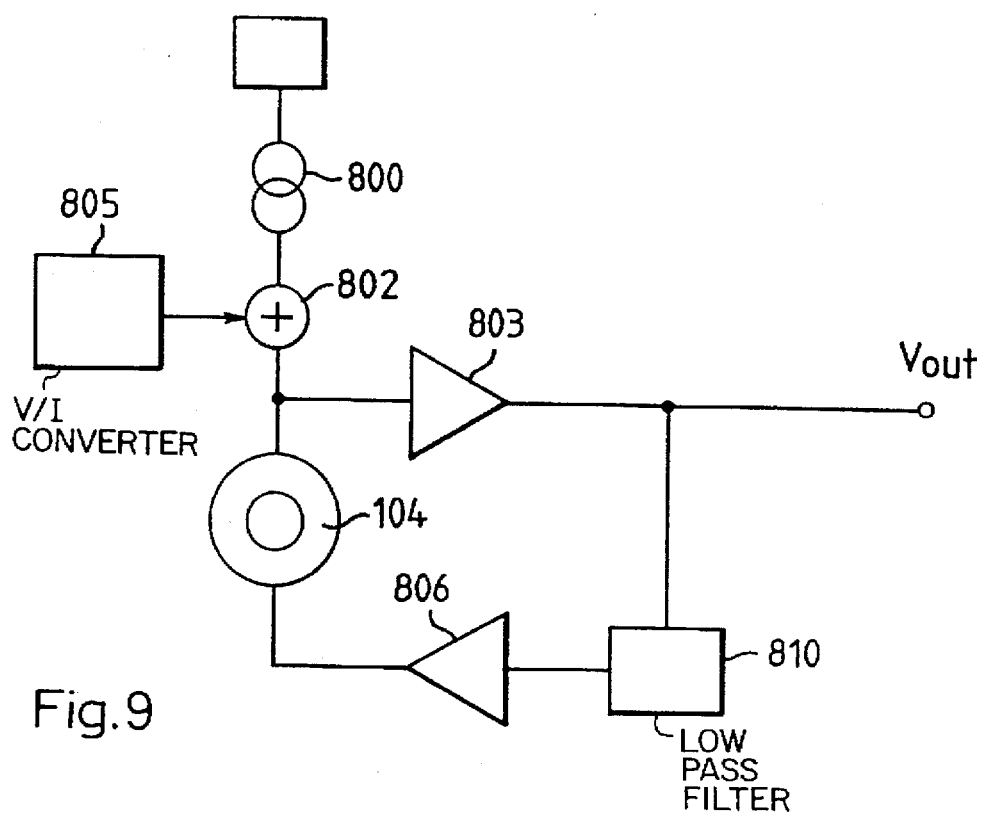
FIG. 9 is a block diagram of a modified version of the alternative embodiment of FIG. 8.

A modified version of this alternative embodiment of pulse generator and constant current source is shown in FIG. 9, with the same components bearing the same reference numerals. In this version, a low pass filter 810 is provided between high gain amplifier 803 and amplifier 806. This modified version uses negative feedback to remove the direct current component. The feedback is low pass filtered in low pass filter 810 to remove signals below about 1 kHz. This allows amplifier 803 to have a high gain (Gain=100) with cross coupling of the two amplifiers 803 and permits a fast recovery from transients. The benefit of a high gain first stage is an improvement in the signal to noise ratio of the differential gain.

It will be appreciated that circuitry analogous to that shown in FIGS. 8 and 9 could be employed to produce a constant voltage and a voltage pulse. Typically the power applied to a cell is in the range of 0.2–1 mA. Powers in excess of this could damage a cell, but maybe used with dead cells or non-biological samples.

In a further alternative version of FIG. 8, it may be possible to use a transconductance amplifier instead of the constant current source 800 and voltage to current converter 805. Use of a transconductance amplifier (either monolithic, discrete or operational amplifier topology) allows the generation of high frequency current signals. However, in the devices currently available, noise is a problem.

The Differential Amplifier (212)

The input signal to the differential amplifier has two components. The first is the high frequency high voltage signal generated by the pulse generator 202, which may be of the order of 30V. The second is due to the response to the signal generated by the pulse generator and may be of the order of only 1 mV. The differential amplifier has to be able to reject the high voltage pulse whilst accepting the low voltage response to it. Thus, since the high frequency high voltage signal generated by the pulse generator is a common mode signal, the amplifier has to have a very good high frequency common mode rejection ratio. Furthermore, the amplifier needs to be wideband, in order to cover the spectrum of the response, but also low noise. These two requirements are conflicting, since noise increases as the square root of bandwidth.

Figure 6:
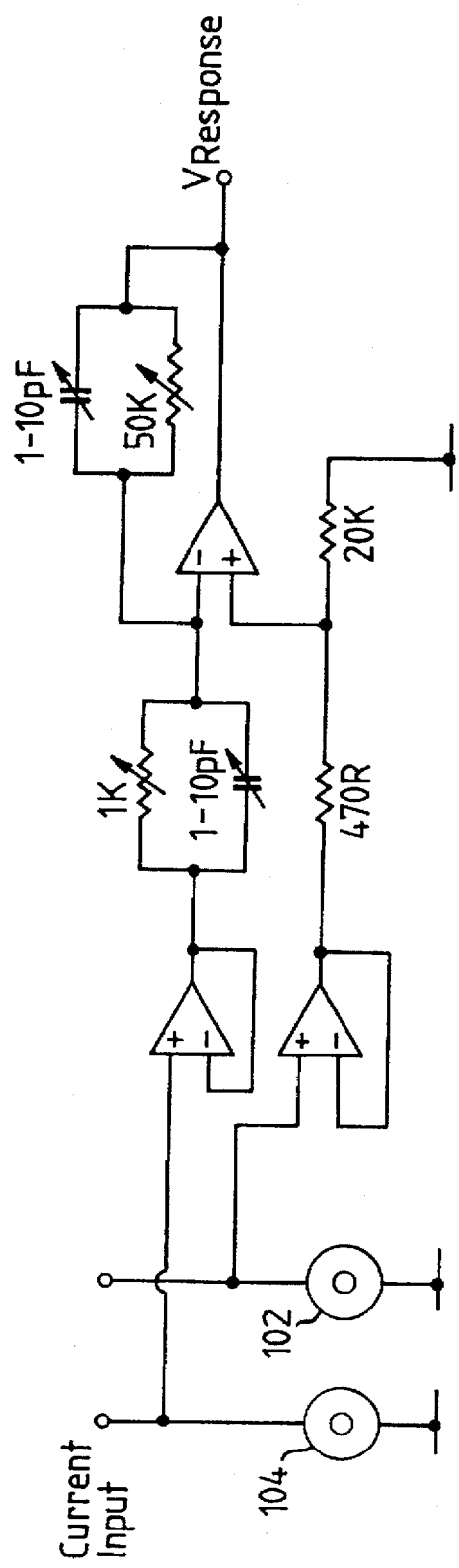
FIG. 6 is a current diagram of a differential amplifier employed in the present invention.

One possible implementation of the differential amplifier is shown in FIG. 6. The differential amplifier 212 includes the live and reference test devices 102 and 104, operational amplifiers IC3, IC4 and IC5 together with their associated circuitry, and RC networks Z1 and Z2. The input to IC3 from the reference test device 104 is $V_p$ (the voltage due to the orifice impedance), whilst the input to IC4 is $V_p$ and also $V_c$ (the voltage due to the cell impedance). Additionally, since there will always be at least a slight difference in impedance between the two test devices, a voltage $V_o$ due to that impedance difference will arise. This is considered as applied to the input of IC3. Amplifiers IC3 and IC4 function as unity gain buffers, whilst amplifier IC5 is a differential amplifier. The two RC networks serve the dual purpose firstly of providing variable compensation for the impedance imbalance of the two test devices and secondly of providing variable passband filtering. In the present embodiment, bandwidths of between 100 kHz and 1 MHz have been used. Thus, the output of the differential amplifier 212 depends on the impedance of the cell and any uncompensated imbalance between the test devices.

As with the pulse generator 202, all the operational amplifiers in the differential amplifier are low noise devices; again, an analogous circuit to that in FIG. 6 may be used if a voltage pulse is employed.

If a four electrode system is used, the two output detector electrodes of each test device 102, 104 could be connected to the respective inputs of two further differential amplifiers (one for each test device). The respective outputs of these amplifiers would then be connected to the unity gain buffers provided by amplifiers IC3 and IC4.

A possible alternative embodiment of differential amplifier would use a number of bandpass filters to separate the frequency spectrum into a number of bands, and a corresponding number of individual differential amplifier units, each one receiving a signal from a respective one of the filters. This arrangement would have an enhanced signal to noise ratio.

The Data Acquisition System (214)

The Data acquisition system is an AMPICON PC99 or SIGNATEC DASP 100A (Trade Mark) system, which is a PC based card with two input channels and a maximum sampling rate of 25 MHz or 100 MHz respectively with 8 bit resolution. In the present embodiment, sampling usually takes place as fast as possible and at least at 20 MHz.

The Computer (216)

The computer 216 is employed to store, analyze and display the data. Analysis proceeds as follows. The process of cell impulse response measurement can be modelled using systems theory. It is well known that the output y(t) of an analog system equals the convolution of the input x(t) with the transfer function h(t) of the system. That is:

$$y(t) = \int_{-\infty}^{+\infty} h(\tau - t) x(t) dx \qquad \text{Equation 1}$$

The equivalent expression can be found in the frequency domain:

$$Y(j\omega) = H(j\omega) X(j\omega) \qquad \text{Equation 2}$$

where $Y(j\omega)$ is the output signal transfer function, $X(j\omega)$ is the input signal transfer function, and $H(j\omega)$ is the system transfer function.

This latter equation can be derived from the former by Fast Fourier Transform techniques. If the input x(t) is a true (ideal) impulse, the Fourier transform ($Y(j\omega)$) of the measured response output (y(t)) is directly the system transfer function ($H(j\omega)$) since the impulse input (x(t)) has a transfer function of unity.

Even if the input x(t) is not an impulse, it is still possible to evaluate the system transfer function $H(j\omega)$, although such evaluation can become computationally involved. However, for a pulse sufficiently close to a true impulse it can be shown that h(t) approximates the area under the pulse, so that in this event evaluation of $H(j\omega)$ is still relatively straightforward.

In evaluating the response due to the cell from the response output y(t), the external influences (namely the test device) as well as the cell itself have to be taken into account. Thus, the response output y(t) is not the cell's transfer function, but the convolution of the cell characteristics and test device characteristics. The test device characteristics are predetermined by a series of frequency sweeping tests. Then, if the test device transfer function determined from these tests is $H_2(j\omega)$, and the cell transfer function is $H_1(j\omega)$, the following relationship can be established for a true impulse:

$$H_1(j\omega) = Y(j\omega)/H_2(j\omega) \qquad \text{Equation 3}$$

Thus the computer 216 is programmed to evaluate the transfer function of the cell by performing a Fast Fourier Transform on y(t) and dividing that by the predetermined $H_2(j\omega)$.

Once the cell transfer function has been evaluated, the various characteristics of the cell can be determined by reference to an appropriate electrical impedance model of the cell. Such information may be stored on RAM at computer 216.

The Cell Position Detector Circuitry (218)

Figure 3A:
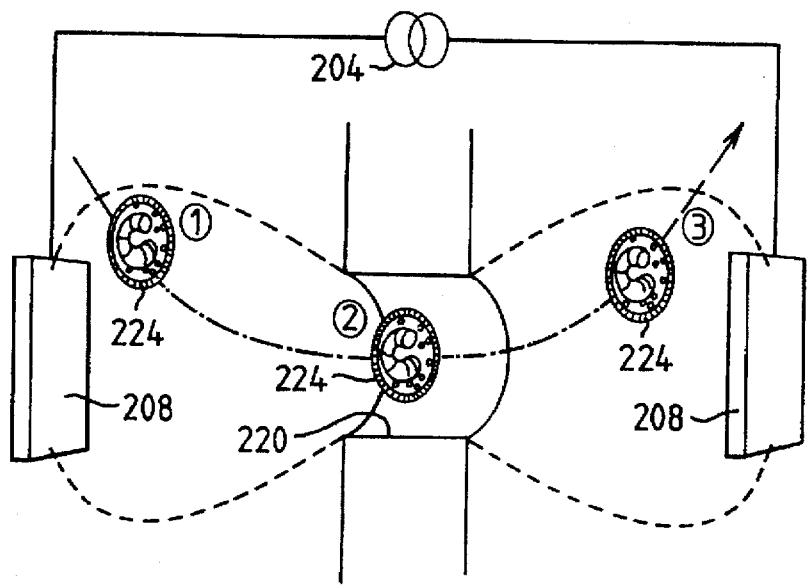
FIG. 3a is a schematic view of an orifice, through which cells pass.
Figure 3B:
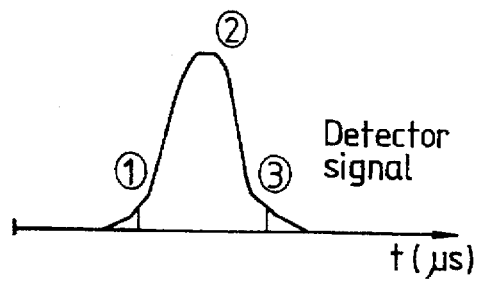
FIGS. 3b to 3d are timing diagrams showing the operation of the present invention.
Figure 3C:
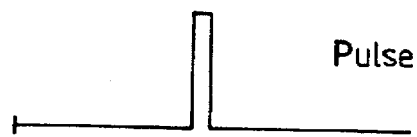
Figure 3D:
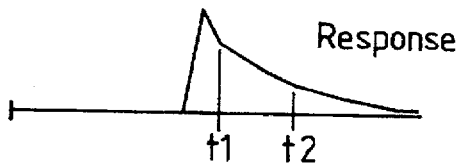
Figure 3E:
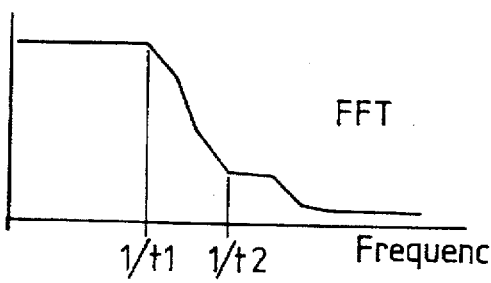
FIG. 3e is a spectral response diagram showing the operation of the present invention.

The cell position detector circuitry 218 serves to generate a trigger pulse for the pulse generator 202. The detector circuitry operates by monitoring the differential voltage output from the two test devices 102 and 104 as a result of the application of the low level direct current (0.2 mA) from the constant current sources 204 and 206. This voltage output is shown in FIG. 3(b). As the cell enters the orifice of the live test device 102, a small voltage peak is observed, the actual peak corresponding to the middle of the orifice. A conventional peak detector would recognize the peak only after it has occurred. Since it is important that the trigger pulse be produced actually as the peak is occurring, the detector circuitry uses a modified technique for detecting the peak. The gradient of the rising edge of the pulse is determined and monitored, and the trigger pulse is produced when this gradient approaches zero.

Figure 7A:
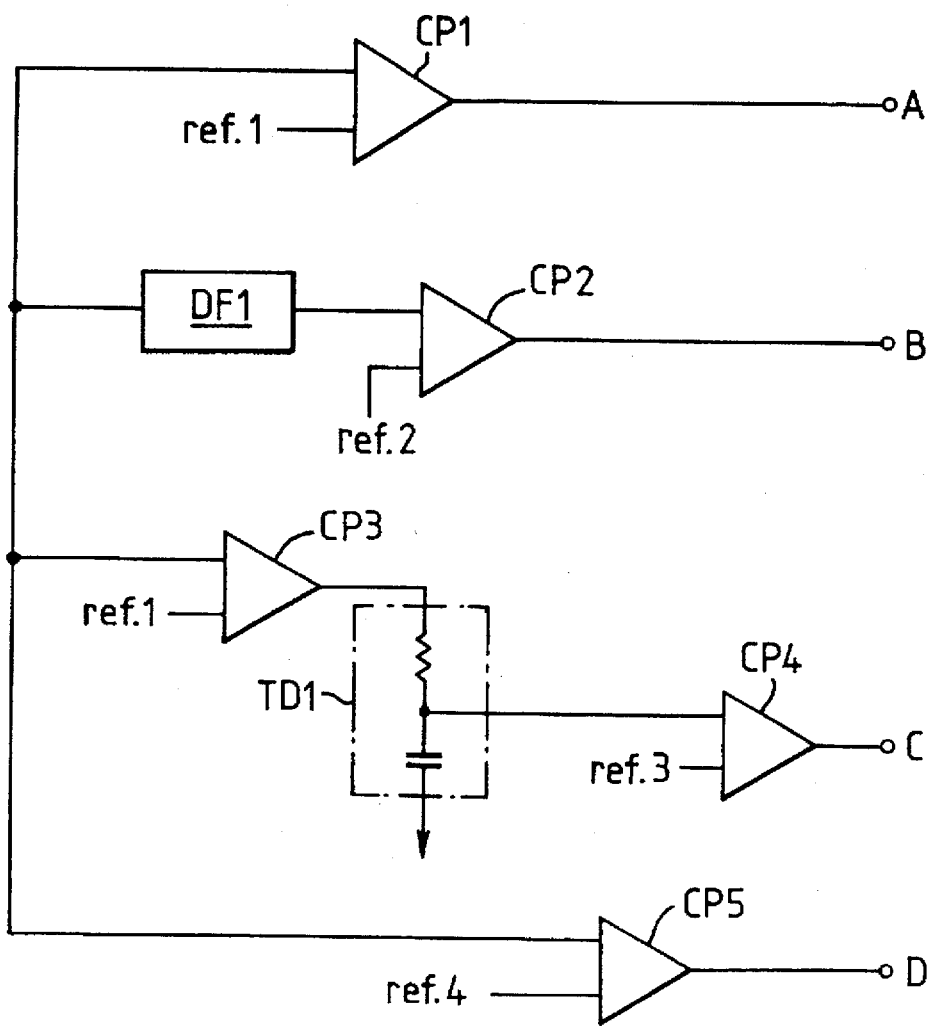
FIGS. 7a and 7b are block diagrams of the two parts of the cell position detector circuitry employed in the present invention.
Figure 7B:
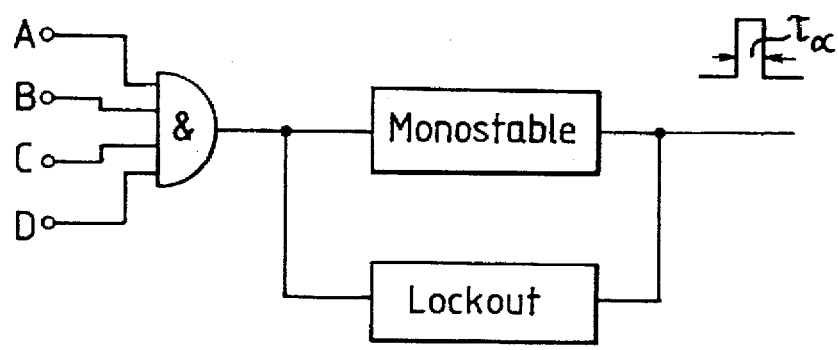

FIGS. 7a and 7b show suitable circuitry for putting these functions into effect. The circuitry comprises comparators CP1, CP2, CP3, CP4 and CP5, a differentiator DF1, a time delay TD1, an AND gate, a MONOSTABLE and a LOCK-OUT.

Referring to FIG. 7a, comparator CP1 produces a minimum amplitude threshold signal at output A if the monitored differential output from the test devices rises above a minimum amplitude threshold (ref. 1). This serves to prevent the cell position detector circuitry 218 triggering on noise. Comparator CP2 takes the voltage differentiated by differentiator DF1 and produces a gradient threshold signal at output B if the voltage gradient falls below a gradient threshold (ref. 2). The gradient threshold is predetermined experimentally such that, when allowance has been made for the time delays which inevitably arise in the circuitry, the trigger pulse is generated at the peak value of the monitored voltage. Comparators CP3 and CP4, and time delay circuit TD1 (producing a time delay of perhaps between 2 and 10 μs which can be set using ref. 3), produce a timer threshold signal at output C. They serve to prevent early firing of the pulse on noise, interference or electrical pulses due to non-axial movement of cells through the orifice, by ensuring that the minimum amplitude threshold (ref. 1) is exceeded for the duration of the time delay. Comparator CP5 produces a maximum amplitude threshold signal at output D if the monitored voltage is below a maximum amplitude threshold (ref. 4). This prevents the detector circuitry 218 being triggered by an excitation pulse, or air bubbles, dirt or other such items. The various thresholds referred to above depend on the type of test device being used and can be determined experimentally.

Referring now to FIG. 7b, the remainder of the cell position detector circuitry takes the outputs A, B, C and D and processes them through the AND gate. The output of the AND gate will be a pulse of unpredictable width. The MONOSTABLE functions to produce a trigger pulse of fixed width $\tau_\alpha$ for passing to the pulse generator 202. The LOCKOUT prevents a second excitation pulse from being triggered until the response from the previous cell has been detected. The LOCKOUT time could vary from, say 20 µs to 100 ms, but is preferably relatively short (30–100 µs) to facilitate a reasonable cell flow rate.

EXAMPLE

The manner in which the present invention may be applied in practice will now be exemplified. There is particular interest in applying the present invention to the investigation of the electrical properties of erythrocytes. Erythrocyte consists of a complex aqueous solution called haemoglobin and a flexible cell membrane. The haemoglobin is contained within the membrane. A linear circuit may be used as the electrical impedance model of the erythrocyte. In this circuit, the model parameters are:

Cd—capacitance of the cell membrane;
Rm—low frequency ion pathways;
Ca, Ra—components of the $\alpha$ dispersion; and
Ri—resistance of the cytoplasm.

In the model, Cd, Rm and the series combination of Ca and Ra are combined in parallel, and this parallel combination is linked in series with Ri. Similar linear models could be constructed for other cells. The values of the model parameters can be evaluated using the spectral response information generated by the present invention.

The cell model may be simplified by considering the membrane as a thin capacitive shell and the cytoplasm as a sphere of highly conductive liquid, so that the model consists of just a resistor and capacitor in parallel. Using this model, it has proved possible with the present invention to discriminate between erythrocytes, leucocytes and mononuclear cells.

Industrial Application

It is envisaged that the invention has utility mainly in the medical field, for example in:
(1) the vascular field, in the examination of blood cells to detect changes;
(2) oncology, in examining cancer cell samples in suspension;
(3) white cell activation due to the immune system or inflammatory processes arising from circulation in the lymph or blood systems;
(4) the therapeutic field, in that abnormal cells can be eliminated after detection; and
(5) measurements on liposomes, or more generally even colloids or powders or even nematodes.

It will be appreciated that the invention has been described above purely by way of example, and modifications of detail can be made within the scope of the invention. For example the invention may be modified for use in sample analysis of chemicals in a laboratory environment. The invention may be used in industries such as food processing, mining, oil exploration, synthetic plastic manufacture or indeed any environment in which a particle to be analysed can be suspended in a fluid. Alternatively or in addition other types of transform may be used instead of Fourier Transforms. Similarly additional electrodes may be provided. A voltage can be established across these electrodes as an "AC biassing" or guard voltage to protect against coupling losses which may occur through the solution supporting the sample.

What is claimed is:

1. A method of determining a distinctive property of a sample, comprising steps of:

applying an electrical pulse to an electrode arrangement across said sample in an electrolyte, said sample being transportable relative to said electrode arrangement, and said electrical pulse having an ON duty cycle of less than 20%;

detecting a response to said electrical pulse;

applying a transform to said detected response; and determining said distinctive property of said sample from said transform of said detected response.

2. A method of determining a distinctive property according to claim 1, wherein:

said distinctive property is an electrical property.

3. A method of determining a distinctive property according to claim 1 or 2, wherein:

said sample includes a cell.

4. A method of determining a distinctive property according to claim 1, wherein:

said electrode arrangement applies said electrical pulse and senses said response.

5. A method of determining a distinctive property according to claim 4, comprising a further step of:

detecting a position of said sample relative to said electrode arrangement;

said electrical pulse being applied in dependence on said detected position of said sample.

6. A method of determining a distinctive property according to claim 4 or 5, wherein:

said sample is a particle;

an orifice is provided through which said particle is transported; and said electrode arrangement is located so as to enable said electrical pulse to be applied to said particle as said particle is transported through said orifice.

7. A method of determining a distinctive property according to claim 6, wherein:

a first duration of said electrical pulse is less than 20% of a second duration of said transportation of said particle through said orifice.

8. A method of determining a distinctive property according to claim 1, wherein said step of detecting said response includes steps of:

determining a first response to said electrical pulse in an absence of said sample; and determining a second response to said electrical pulse in a presence of said sample;

said second response to said electrical pulse includes a first component due to said sample itself and a second component due to influences external to said sample, said first component being determined from a difference between said second response and said first response.

9. Apparatus for determining a distinctive property of a sample, comprising:

means for applying an electrical pulse to said sample, said electrical pulse having an ON duty cycle of less than 20%;

means for detecting a response to said electrical pulse;

means for applying a transform to said detected response; and means for determining said distinctive property of said sample from said transform of said detected response;

said sample being transportable in an electrolyte relative to said means for applying said electrical pulse.

10. Apparatus for determining a distinctive property of a sample according to claim 9, wherein:

said distinctive property is an electrical property.

11. Apparatus for determining a distinctive property of a sample according to claim 9, further including:

an electrode arrangement by which said electrical pulse is applied and said response is detected.

12. Apparatus for determining a distinctive property of a sample according to claim 11, further comprising:

means for detecting a position of said sample relative to said electrode arrangement;

said means for applying said electrical pulse being arranged to apply said electrical pulse in dependence on said detected position of said sample.

13. Apparatus for determining a distinctive property of a sample according to claim 11 or 12, said apparatus further comprising:

an orifice through which said particle is transportable; and said electrode arrangement being located so as to enable said electrical pulse to be applied to said particle as said particle is transported through said orifice.

14. Apparatus for determining a distinctive property of a sample according to claim 13, wherein:

a first duration of said electrical pulse is less than 20% of a second duration of said transportation of said particle through said orifice.

15. Apparatus for determining a distinctive property of a sample according to claim 9, wherein said means for detecting said response to said electrical pulse comprises:

means for determining a first response to said electrical pulse in an absence of said sample, for determining a second response to said electrical pulse in a presence of said sample, and for determining a component of said second response due to said sample from a difference between said second response and said first response.

16. Apparatus for determining a distinctive property of a sample according to claim 15, wherein said means for determining includes:

a reference test device; and a live test device;

said means for determining being arranged to determine said first response and said second response simultaneously in said reference test device and said live test device, respectively.

17. Apparatus for determining a distinctive property of a sample according to claim 9, further comprising:

material having a low dielectric constant being interposed between an inner two electrodes of said electrode arrangement.

18. Apparatus for determining a distinctive property of a sample according to claim 17, wherein:

a ratio of a thickness of said material to a distance between said inner two electrodes is greater than 25%.

19. Apparatus for determining a distinctive property of a sample according to claim 9, wherein:

a ratio of an area of one of an electrode pair of said electrode arrangement to a separation of electrodes of said electrode pair is less than 500.

20. Apparatus for determining a distinctive property of a sample according to claim 13, wherein said means for detecting said response of said electrical pulse includes:

two electrodes mounted at opposite ends of said orifice.

21. A method of determining a distinctive property according to claim 8, wherein:

said second component due to influences external to said sample is indicative of a characteristic of said orifice.

22. A method of determining a distinctive property according to claim 6, wherein:

a first duration of said electrical pulse is less than 10% of a second duration of said transportation of said particle through said orifice.

23. Apparatus for determining a distinctive property of a sample according to claim 13, wherein:

a first duration of said electrical pulse is less than 10% of a second duration of said transportation of said particle through said orifice.

24. Apparatus for determining a distinctive property of a sample according to claim 17, wherein:

a ratio of a thickness of said material to a distance between said inner two electrodes is greater than 50%.

25. Apparatus for determining a distinctive property of a sample according to claim 9, wherein:

a ratio of an area of one of an electrode pair of said electrode arrangement to a separation of electrodes of said electrode pair is less than 200.

26. Apparatus for determining a distinctive property of a sample according to claim 9, wherein:

a ratio of an area of one of an electrode pair of said electrode arrangement to a separation of electrodes of said electrode pair is less than 100.

27. Apparatus for determining a distinctive property of a sample according to claim 9, further comprising:

two electrodes with a dielectric substance therebetween, said two electrodes being in contact with said sample.

28. Apparatus for determining a distinctive property of a sample according to claim 9, wherein:

said means for applying an electrical pulse includes two outer electrodes with a dielectric substance therebetween; and said means for detecting said response to said electrical pulse includes two inner electrodes.

29. Apparatus for determining a distinctive property of a sample according to claim 28, wherein:

said two inner electrodes form a portion of an orifice through which said sample is transportable in said electrolyte.

30. Apparatus for determining a distinctive property of a sample according to claim 9, wherein:

said electrical pulse applied by said means for applying is a square pulse.

31. Apparatus for determining a distinctive property of a sample according to claim 9, wherein:

said electrical pulse is 2 µs to 5 µs wide.

32. Apparatus for determining a distinctive property of a sample according to claim 9, wherein:

said electrical pulse is 2 µs wide.

33. Apparatus for determining a distinctive property of a sample according to claim 9, wherein:

said electrical pulse is 0.5 to 5 mA in amplitude.

34. Apparatus for determining a distinctive property of a sample according to claim 9, wherein:

said electrical pulse is 3 mA in amplitude.

35. Apparatus for determining a distinctive property of a sample according to claim 9, wherein:

said electrical pulse has a rise time and a fall time on the order of 20 to 40 nS.

36. Apparatus for determining a distinctive property of a sample according to claim 9, wherein:

said reference test device and said live test device are arranged into a bridge configuration.

37. A method of determining a distinctive property of a sample according to claim 1, wherein:

said applied electrical pulse is a square pulse.

38. A method of determining a distinctive property of a sample according to claim 1, wherein:

said electrical pulse is 2 µs to 5 µs wide.

39. A method of determining a distinctive property of a sample according to claim 1, wherein:

said electrical pulse is 2 µs wide.

40. A method of determining a distinctive property of a sample according to claim 1, wherein:

said electrical pulse is 0.5 to 5 mA in amplitude.

41. A method of determining a distinctive property of a sample according to claim 1, wherein:

said electrical pulse is 3 mA in amplitude.

42. A method of determining a distinctive property of a sample according to claim 1, wherein:

said electrical pulse has a rise time and a fall time on the order of 20 to 40 nS.

43. A method of determining a distinctive property of a sample according to claim 1, wherein:

said electrical pulse is triggered only when said sample is in a middle of an orifice.

44. A method of determining a presence of an abnormality in a sample, comprising steps of:

applying an electrical pulse to a sample through an electrode pair, said sample being transportable relative to said electrode arrangement, and said electrical pulse having an ON duty cycle of less than 20%;

detecting a response to said electrical pulse;

applying a transform to said detected response; and determining said presence of said abnormality in said sample based on said transform of said detected response.

45. Apparatus for determining a presence of an abnormality in a sample, said apparatus comprising:

an electrical pulse generator for applying an electrical pulse having an ON duty cycle of less than 20% to said sample as it is suspended in an electrolyte and transported through an orifice;

a detector for detecting a response to said electrical pulse;

a processor to apply a transform to said detected response, and to determine said presence of said abnormality in said sample based on said transform of said detected response.

46. Apparatus for determining a presence of an abnormality in a sample according to claim 45, wherein:

said electrical pulse generator is triggered to apply said electrical pulse to said sample only when said sample is in an optimal position in said orifice.

47. A method of determining a distinctive property according to claim 1, wherein:

said electrical pulse has an ON duty cycle of less than 10%.

48. Apparatus for determining a distinctive property of a sample according to claim 9, wherein:

said electrical pulse has an ON duty cycle of less than 10%.

49. A method of determining a presence of an abnormality in a sample according to claim 44, wherein:

said electrical pulse has an ON duty cycle of less than 10%.

50. Apparatus for determining a presence of an abnormality in a sample according to claim 45, wherein:

said electrical pulse has an ON duty cycle of less than 10%.

* * * * *